(12) United States Patent  
Chanoch et al.

(10) Patent No.: US 9,345,842 B2  
(45) Date of Patent: May 24, 2016

(54) ADJUSTABLE DOSE SETTING PLUNGER FOR SYRINGE

(75) Inventors: Lawrence H. Chanoch, Mahwah, NJ (US); John B. Wilson, Holly Springs, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 936 days.

(21) Appl. No.: 13/067,631

(22) Filed: Jun. 15, 2011

(65) Prior Publication Data

US 2011/0313396 A1 Dec. 22, 2011

Related U.S. Application Data

(60) Provisional application No. 61/344,257, filed on Jun. 18, 2010.

(51) Int. Cl.
| | |
|---|---|
| *A61M 5/315* | (2006.01) |
| *A61M 5/31* | (2006.01) |
| *A61M 5/32* | (2006.01) |
| *A61M 5/178* | (2006.01) |

(52) U.S. Cl.
CPC ....... *A61M 5/31561* (2013.01); *A61M 5/31551* (2013.01); *A61M 5/1782* (2013.01); *A61M 5/31511* (2013.01); *A61M 5/3202* (2013.01)

(58) Field of Classification Search
CPC ............ A61M 5/31501; A61M 5/31503; A61M 5/31528; A61M 5/3153; A61M 5/31551; A61M 5/31561; A61M 5/31563; A61M 5/3158; A61M 5/31505; A61M 5/31548; A61M 5/3156; A61M 5/31586; A61M 5/31585; A61M 5/31525; A61M 5/31556

USPC ............... 604/211, 218, 220, 224, 227
See application file for complete search history.

(56) References Cited

U.S. PATENT DOCUMENTS

| | | | | | |
|---|---|---|---|---|---|
| 329,403 | A | * | 10/1885 | McAllister | 604/219 |
| 2,254,449 | A | * | 9/1941 | Rasmussen | 604/211 |
| 2,736,315 | A | * | 2/1956 | Feeney | A61M 5/31551 604/211 |
| 3,128,765 | A | * | 4/1964 | Tint | 604/193 |
| 3,253,592 | A | * | 5/1966 | Von Pechmann | 604/222 |
| 3,281,023 | A | * | 10/1966 | Bruck et al. | 222/390 |

(Continued)

FOREIGN PATENT DOCUMENTS

| | | | | |
|---|---|---|---|---|
| DE | 17 98 824 U | | 10/1959 | |
| DE | 1798824 U | * | 10/1959 | ........ A61M 5/31551 |

(Continued)

OTHER PUBLICATIONS

European Search Report issued in Application No. 11170077.9-2320/2397173 dated Aug. 6, 2013.

(Continued)

*Primary Examiner* — Kevin C Sirmons  
*Assistant Examiner* — William Carpenter  
(74) *Attorney, Agent, or Firm* — Dickinson Wright PLLC

(57) ABSTRACT

A syringe includes a body for receiving a medicament and a plunger movably connected to the syringe body. The plunger is moved with respect to the syringe body to draw in and dispense the medicament. A plurality of dose setting indicators are disposed on the plunger. The plunger is rotated outwardly from the syringe body to draw medicament into the syringe body. The plunger can be pushed or rotated into the syringe body to dispense the medicament.

17 Claims, 3 Drawing Sheets

(56) References Cited

U.S. PATENT DOCUMENTS

| | | | |
|---|---|---|---|
| 3,343,539 A * | 9/1967 | Moorhouse | 604/211 |
| 3,353,718 A * | 11/1967 | McLay | 222/158 |
| 3,672,369 A * | 6/1972 | Brown | 604/222 |
| 4,165,646 A | 8/1979 | Shapiro | |
| 4,173,225 A | 11/1979 | Newman | |
| 4,346,708 A | 8/1982 | LeVeen | |
| 4,498,904 A | 2/1985 | Turner | |
| 4,710,179 A | 12/1987 | Haber | |
| RE32,974 E | 7/1989 | Porat | |
| 4,861,335 A * | 8/1989 | Reynolds | 604/88 |
| 4,865,591 A | 9/1989 | Sams | |
| 4,973,318 A * | 11/1990 | Holm et al. | A61M 5/24 604/208 |
| 5,009,645 A | 4/1991 | Silver | |
| 5,104,380 A | 4/1992 | Holman | |
| 5,222,942 A | 6/1993 | Bader | |
| 5,226,896 A | 7/1993 | Harris | |
| 5,304,152 A | 4/1994 | Sams | |
| 5,318,544 A | 6/1994 | Drypen | |
| 5,472,431 A * | 12/1995 | Godat et al. | 604/199 |
| 5,507,727 A * | 4/1996 | Crainich | 604/97.02 |
| 5,531,708 A | 7/1996 | Woodruff | |
| 5,807,346 A | 9/1998 | Frezza | |
| 5,947,934 A | 9/1999 | Hansen | |
| 6,086,567 A | 7/2000 | Kirchhofer | |
| 6,248,090 B1 | 6/2001 | Jensen | |
| 6,368,308 B1 | 4/2002 | Nerney | |
| 6,562,007 B1 | 5/2003 | Falsey | |
| 6,613,023 B2 | 9/2003 | Kirchhofer | |
| 6,793,660 B2 * | 9/2004 | Kerr et al. | 606/93 |
| 7,169,131 B2 | 1/2007 | Gatti | |
| 7,214,213 B2 | 5/2007 | Michel | |
| 7,241,278 B2 | 7/2007 | Moller | |
| 7,297,136 B2 | 11/2007 | Wyrick | |
| 7,329,241 B2 | 2/2008 | Horvath | |
| 7,427,276 B2 | 9/2008 | Tachikawa | |
| 7,621,891 B2 | 11/2009 | Wyrick | |
| 8,038,655 B2 | 10/2011 | Burren | |
| 8,747,367 B2 * | 6/2014 | Keitel et al. | 604/211 |
| 9,073,649 B2 * | 7/2015 | Norton | B01L 3/0293 |
| 2002/0120235 A1 | 8/2002 | Enggaard | |
| 2003/0004467 A1 | 1/2003 | Musick | |
| 2004/0024365 A1 * | 2/2004 | Bonnier | A61M 5/31525 604/189 |
| 2005/0004530 A1 | 1/2005 | Grabenkort | |
| 2005/0015056 A1 | 1/2005 | Duchon | |
| 2005/0215957 A1 | 9/2005 | Hynes | |
| 2006/0129122 A1 | 6/2006 | Wyrick | |
| 2007/0017533 A1 | 1/2007 | Wyrick | |
| 2007/0225656 A1 | 9/2007 | Hoyle, Jr. | |
| 2007/0244444 A1 | 10/2007 | Guelker | |
| 2008/0097322 A1 | 4/2008 | Markussen | |
| 2008/0171995 A1 * | 7/2008 | Vitullo | A61M 5/28 604/187 |
| 2009/0264828 A1 * | 10/2009 | Dette | A61M 5/31533 604/189 |

FOREIGN PATENT DOCUMENTS

| | | |
|---|---|---|
| EP | 0178023 | 4/1986 |
| EP | 2 050 477 | 4/2009 |
| JP | 58-500648 | 4/1983 |
| JP | 2004538100 A | 12/2004 |
| JP | 2007509662 A | 4/2007 |
| WO | 95/11711 | 5/1995 |
| WO | 2004/016303 | 2/2004 |

OTHER PUBLICATIONS

European Search Report issued in Application No. 11170077.9-2320/2397173 dated Dec. 12, 2012.

Japanese Office Action issued in Japanese application No. 2011-136309 dated Mar. 24, 2015.

* cited by examiner

ADJUSTABLE DOSE SETTING PLUNGER FOR SYRINGE

CROSS-REFERENCE TO RELATED APPLICATION

This application claims the benefit under 35 U.S.C. §119 (e) of U.S. provisional patent application Ser. No. 61/344,257, filed Jun. 18, 2010, the entire disclosure of which is hereby incorporated by reference.

FIELD OF THE INVENTION

The present invention relates generally to a syringe having an adjustable dose setting plunger to selectively control dosage. More particularly, the present invention relates to a plunger that is rotated to draw the desired dose of a liquid medicament into a syringe. Still more particularly, the present invention relates to a syringe plunger having dose settings indicated on the plunger to facilitate drawing the desired dose into the syringe.

BACKGROUND OF THE INVENTION

Users of existing syringes generally must visually measure the medication level being drawn from a container into the syringe using scale markings while the dose is being drawn. The plunger is drawn axially and rearwardly through a cylindrical tube, or barrel, of the syringe to create suction within the barrel to draw liquid medication from a container into the syringe. The axial distance the plunger moves rearwardly determines the volume of the medication drawn into the syringe. The medication is then dispensed by moving the plunger forward through the barrel. The scale markings on the barrel facilitate the user drawing the desired dosage.

The amount of dose is determined by the volume of liquid medication drawn into the syringe, and the scale markings run perpendicularly to the longitudinal axis of the syringe. The scale markings and graduation lines are typically closely spaced. Thus, the scale markings can be difficult to read, making drawing an accurate dose difficult. Accordingly, a need exists for a syringe in which the dose setting is easily viewable and determinable.

Furthermore, a precise dose requires the piston to be moved a small distance. The break-away (static friction) required to begin plunger movement is greater than the glide-force (dynamic friction) required once the plunger has begun moving. Thus, it is easy for a user to over-shoot a desired dose setting when precise movement is required, which often results in the user repeatedly moving the plunger above and below the desired dose setting. Accordingly, a need exists for a syringe in which the desired dosage is easily obtainable.

The user ultimately determines the amount of liquid medication drawn into the syringe. Thus, when the user is not being careful, too little or too much medication can be drawn into the syringe. Accordingly, a need exists for a syringe in which an accurate dose is easily drawn into the syringe.

SUMMARY OF THE INVENTION

In accordance with an aspect of the present invention, a syringe is provided with an adjustable dose setting plunger to control dosage.

In accordance with another aspect of the present invention, a syringe has a plunger that is rotated with respect to the syringe body to draw in a dose of a liquid medicament.

In accordance with yet another aspect of the present invention, a syringe has dose setting indicators disposed on the plunger to facilitate drawing in an accurate dose.

Several advantages are achieved by eliminating the need for scale marking on the syringe. The syringe barrel can be shorter and wider, thereby allowing the overall length of the syringe to be shortened. Only the selected dose setting number can be made visible to the user, thereby providing an easy-to-use syringe. The dose setting number may be oriented along the axis of the syringe, thereby providing easier and improved viewing of the dose setting.

In accordance with an aspect of the present invention, a syringe includes a body for receiving a liquid medicament and a plunger rotatably movable with respect to the body to set a dose and draw the liquid medicament into the body.

In accordance with another aspect of the present invention, a syringe includes a body for receiving a liquid medicament, a flange assembly fixedly disposed in the body and a plunger movably connected to the flange assembly. The flange assembly includes a flange, a wall extending downwardly from the flange and a bore extending through the flange assembly. The plunger is moved with respect to the flange assembly to draw in and dispense the liquid medicament. A plurality of dose setting indicators are disposed on the plunger.

In accordance with another aspect of the present invention, a method of operating a syringe includes rotating a plunger outwardly from a syringe body to set a dose and draw medicament into the syringe. Rotation of the plunger is stopped when a desired dose setting is obtained.

Objects, advantages, and salient features of the invention will become apparent from the following detailed description, which, taken in conjunction with the annexed drawings, discloses exemplary embodiments of the invention.

As used in this application, the terms "front," "rear," "upper," "lower," "upwardly," "downwardly," and other orientational descriptors are intended to facilitate the description of the exemplary embodiments of the present invention, and are not intended to limit the structure thereof to any particular position or orientation.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF EXEMPLARY EMBODIMENTS

In an exemplary embodiment of the present invention, as shown in FIGS. 1-7, a syringe 111 includes a syringe body 121, a flange assembly 141 disposed in the syringe body, and a plunger 161 movably received by the flange assembly. All of these components are preferably made of suitable plastic material(s).

Figure 1:
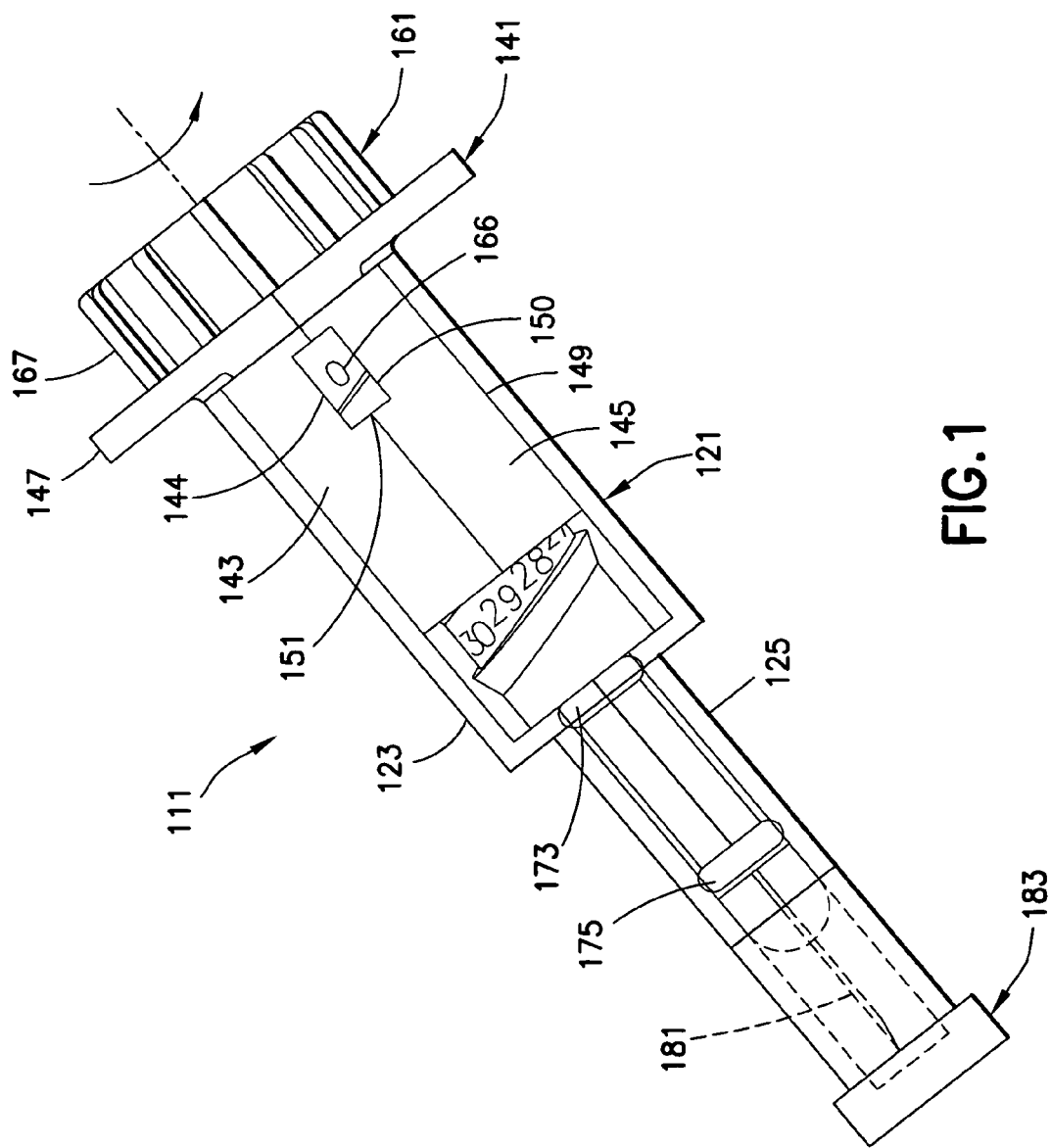
FIG. 1 is a perspective view of a syringe in accordance with an exemplary embodiment of the present invention.
Figure 2:
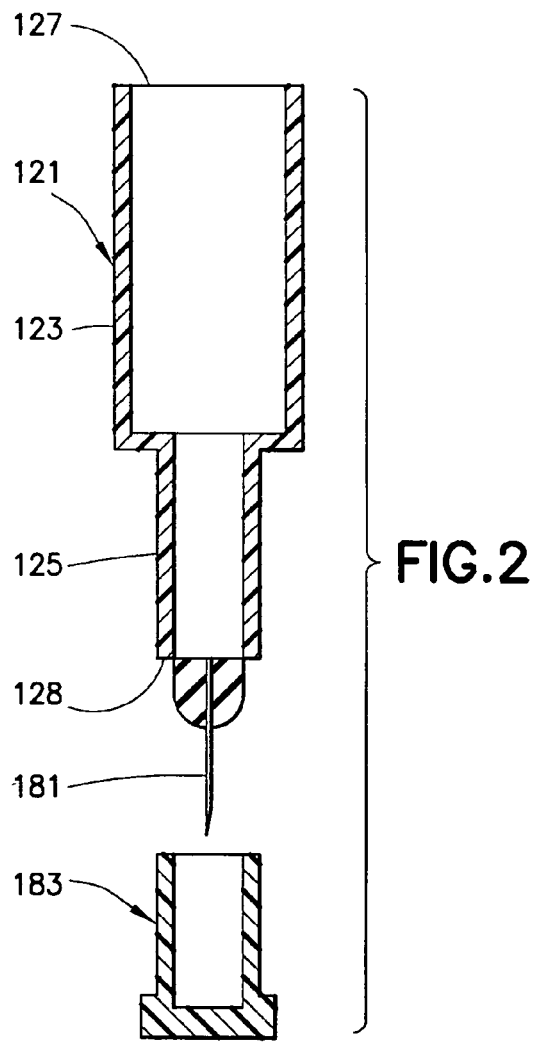
FIG. 2 is a front elevational view in cross section of a syringe body of the syringe of FIG. 1.
Figure 3:
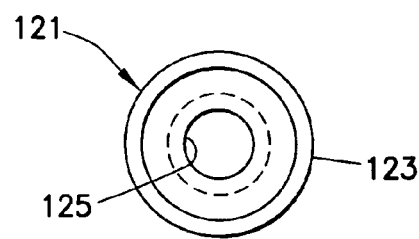
FIG. 3 is a top plan view of the syringe body of FIG. 2.

The syringe body 121 has a first part 123 having a first diameter and a second part 125 having a second diameter, as shown in FIGS. 1 and 2. Preferably, the first diameter of the first part 123 is larger than the second diameter of the second part 125. The second part 125 receives medication drawn in by the syringe. The first part 123 preferably has a larger diameter to allow space for the dose setting indicators. The syringe has a first end 127 and a second end 128. Preferably, the syringe body 121 is transparent such that a user can view the medication in the second part 125 and the dose setting indicator 166 displayed in the window 151 of the first part 123, as shown in FIG. 1. The syringe body 121 is preferably unitarily formed as a single piece as shown in FIG. 2.

Figure 4:
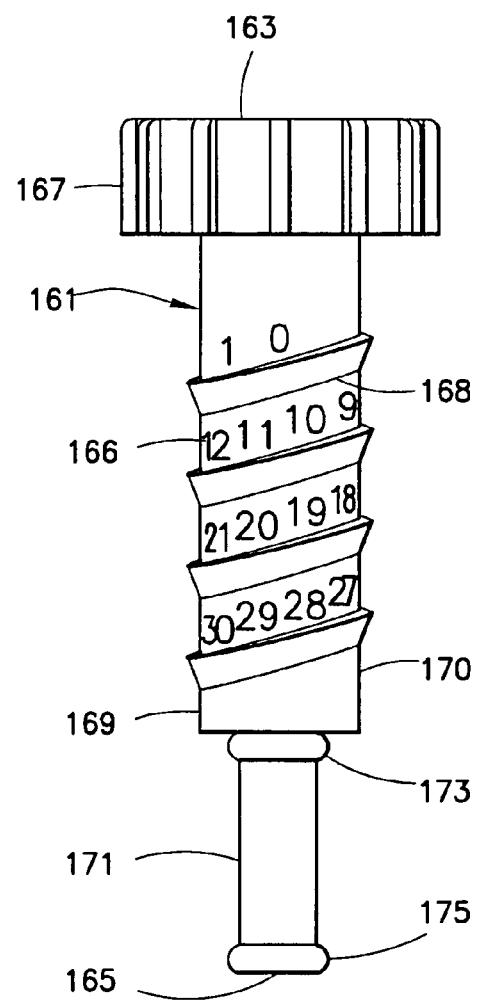
FIG. 4 is a front elevational view of a plunger of the syringe of FIG. 1.

The plunger 161 includes a dose knob 167, a sealing portion 171 and a dose setting portion 169 connected therebetween, as shown in FIG. 4. The dose knob 167 is disposed at a first end 163 of the plunger 161. The dose knob 167 is larger than the bore in the flange assembly 141 to prevent the dose knob from entering the bore. The sealing portion 171 has a first seal member 173 and a second seal member 175. The second seal member 175 is disposed at a second end 165 of the plunger 161. The first seal member 173 maintains sterility of the first portion 123 of the syringe body 121, as shown in FIG. 1. The second seal member 175 provides the suction to draw medication from a container into the syringe 111. When the plunger 161 is in a first position, as shown in FIG. 1, the second seal member 175 abuts the lower end of the second part 125 of the syringe body 121. As the plunger 161 is rotated out of the syringe body 121, the second seal member 175 moves away from the second end 128 of the syringe body 121, thereby creating a suction to draw medication into the second part 125 of the syringe body 121.

An outer surface 170 of the dose setting portion 169 of the plunger 161 has threads 168 disposed thereon that engage the corresponding threads 148 of the flange assembly 141. A plurality of dose setting indicators 166 are printed on the outer surface 170 of the dose setting portion 169 of the plunger 161. The dose setting indicators 166 correspond to the position of the plunger 161, and thus, the dose setting. Preferably, the dose setting indicators 166 are numeric values corresponding to the number of units of medication drawn into the syringe 111. The dose setting indicators 169 are preferably disposed on top of the threads 168, as shown in FIG. 4. Rib and detent means may be included on the outer surface 170 of the plunger 161 and the inner surface 146 of the flange assembly 141 to facilitate selection of dose increments consistent with the increments and integers provided on the plunger 161. The dose setting indicator 166 may be digitally displayed in the window 151, thereby providing an easy to read output for the user.

Figure 5:
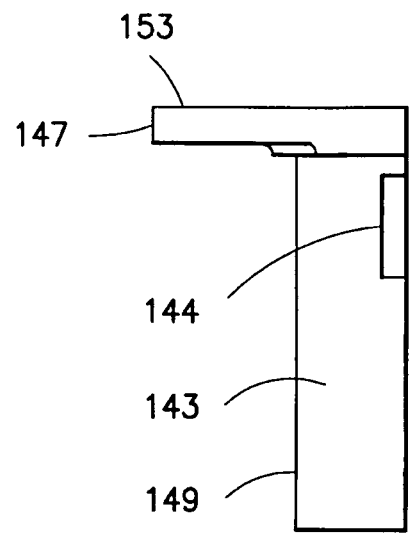
FIG. 5 is a side elevational view of one of the two flange members of the syringe of FIG. 1.
Figure 6:
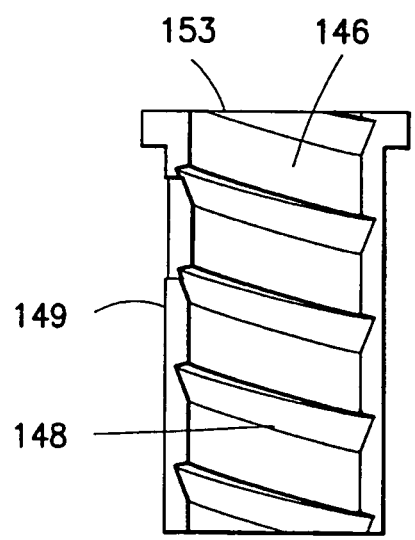
FIG. 6 is a front elevational view of the flange member of FIG. 5.
Figure 7:
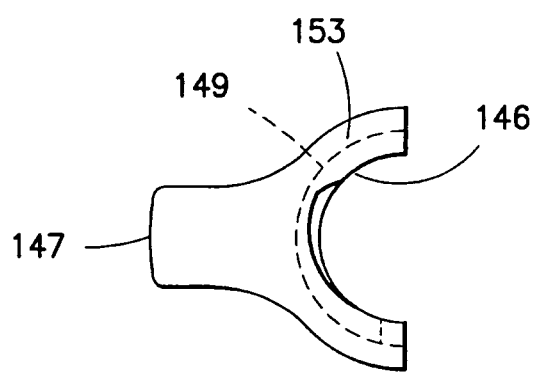
FIG. 7 is a top plan view of the flange member of FIG. 5.

The flange assembly 141 preferably includes first and second flange members 143 and 145, as shown in FIG. 1. Preferably, the first and second flange members 143 and 145 are substantially mirror opposites. As shown in FIGS. 5-7, each flange member is substantially semi-circular, as shown in FIG. 7. The flange member 143 has a handle 147 disposed at an upper end 153 to limit insertion of the flange member into the syringe body 121. A wall 149 extends downwardly from the handle 147. An inner surface 146 of the wall 149 has threads, as shown in FIG. 6, to engage corresponding threads of the plunger 161. The wall 149 of the flange member 143 has a cutout 144, as shown in FIG. 5, that is disposed proximal a cutout 150 in the second flange member 145 to form a window 151, as shown in FIG. 1. The flange assembly 141 is immovably disposed in the first part 123 of the syringe body 121, as shown in FIG. 1. Preferably, the flange assembly 141 is a press fit or an interference fit within the first part 123 of the syringe body 121. The inner surfaces 146 of the walls 149 of the flange members 143 and 145 form a bore through the flange assembly 141 when the first and second flange members are disposed in the syringe body 121. Alternatively, the flange assembly 141 can be unitarily formed. Alternatively, the threads can be formed on an inner surface of the syringe body 121 such that the flange assembly 141 is not required.

A needle 181 is connected to the syringe body 121 at the second end 128 thereof. Preferably, the needle 181 is integrally attached to the syringe body 121. Medication is drawn from a container through the needle 181 into the second part 125 of the syringe body 121 and dispensed from the syringe body through the needle, such as into an injection site. The syringe 111 is preferably intended for a single use and is properly disposed of after an injection. A shield 183 may be disposed over the needle 181 and abutting the first end 128 of the syringe body 121 to prevent accidental needle sticks. The exemplary embodiments of the present invention are applicable to any type of syringe, such as an insulin syringe or other type of syringe. The needle 181 may be omitted or may be made removable by means of a Luer connector or the like, to allow the syringe to be used with a port or IV line.

The syringe 111 has a window 151 through which the dose setting is displayed, preferably in large numbers that are easy for a user to see, learn and use. As the user dials in the desired dose, the medicine is drawn into the syringe body 121 by the suction created by rotating the plunger 161 out of the syringe body.

To perform an injection, the desired dose to be injected is dialed in with the dose knob 167. Initially, the first seal member 173 engages the lower end of the first part, or portion, 123 of the syringe body 121, the second seal member 175 engages the lower end of the second part, or portion, 125 of the syringe body, and the dose setting indicator 166 in the window 151 indicates that no medication has been drawn into the syringe body (i.e., the dose setting indicator "0" is shown). The needle 181 is inserted in a container, such as an insulin container, in which the medication to be delivered is stored. The dose knob 167 is rotated out of the syringe body 121, as indicated by the arrow, thereby axially moving the dose setting portion 169 of the plunger 161 out of the syringe body 121. As the dose knob 167 moves out of the syringe body 121, the second seal member 175 moves rearwardly, thereby drawing medication into the second part 125 of the syringe body 121. When the dose indicator 166 corresponding to the desired dose setting appears in the window 151, the desired dose has been drawn into the second portion 125 of the syringe body 121 and the plunger 161 is in a second position. The larger the dose to be delivered, the further the plunger 161 moves out of the syringe body 121, and, accordingly, the farther from the second end 128 of the syringe body 121 the second seal member 175 moves. Rib and detent means facilitate movement between the dose setting indicators 166. A rib disposed on one of the plunger 161 or flange assembly 141 engages detents disposed on the other of the plunger or flange assembly to facilitate movement between dose setting indicators. Engagement between the threads 168 of the plunger 161 and the threads 148 of the flange assembly 141 facilitate rotation of the plunger out of the syringe body 121.

To inject the drawn dose, the plunger 161 is pushed back into the syringe body 121 from the second position until the first and second seal members 173 and 175 return to the first positions, as shown in FIG. 1. In the first position, the first seal member 173 abuts the lower end of the first part 123 of the syringe body 121 and the second seal member 175 abuts the lower end of the second part 125 of the syringe body 121, thereby preventing further inward movement of the plunger 161. The injection is accomplished by axial or linear movement of the plunger 161, i.e., the plunger is not rotated back to the first position. Such axial movement is possible because of the saw-tooth thread profile on the plunger 161 and the plunger threads being thin and somewhat flexible, thereby allowing the required thread deflection to permit disengagement from the flange assembly threads 148, thereby allowing axial ratcheting movement of the plunger 161 with respect to the flange assembly 141 and the syringe body 121. Visual indication of the medication having been injected is provided by the clear plastic material of the second part 125 of the syringe body 121, i.e., the user can see that the second part 125 has been emptied of medication. Alternatively, the plunger 161 can rotate back to the first position.

In accordance with exemplary embodiments of the present invention, a syringe is provided that is simple to use and ensures that the correct dose has been drawn up and delivered. Additionally, a mechanical advantage is provided by the thread engagement between the plunger 161 and the flange assembly 141, thereby requiring a lower start-up force from the user.

The pitch of the threads can be changed to meet specific patient needs. Changing the thread pitch controls the maximum delivery capacity of the syringe 111 and the selectable increments within that capacity. For example, a syringe having a 100 unit capacity and a 2 unit increment can be manufactured with the same manufacturing equipment as a syringe having a 25 unit capacity and a ½ unit increment. Accordingly, a high degree of interchangeability of syringe components is provided in accordance with exemplary embodiments of the present invention. Moreover, a high degree of accuracy is obtainable with a syringe in accordance with exemplary embodiments of the present invention, such as a syringe being adjustable by ½ unit increments, that is difficult to accomplish with existing syringes.

Furthermore, a syringe in accordance with exemplary embodiments of the present invention benefits from a low-cost design compatible with high-volume manufacturing techniques. The syringe has the same number of components as the existing syringes. Accordingly, product costs for the syringe are substantially equivalent to costs associated with manufacturing existing syringes. Additionally, by increasing the accuracy and ease with which the proper dosage is drawn by the syringe, medication costs are reduced.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined by the appended claims and their equivalents.

What is claimed is:

1. A syringe, comprising:
a body for receiving a medicament;
a plunger comprising a first portion rotatably movable with respect to said body to selectively set a dose of said medicament and a second portion axially movable in a first direction with respect to said body to selectively draw said medicament into said body according to said dose;
a thread disposed on a surface of said first portion of said plunger and in rotational engagement with at least a first portion of said body, said thread axially deflecting with respect to said first portion of said body when said plunger is pushed axially with respect to said body in a second direction to dispense said medicament from said body;
a plurality of numerical indicators helically arranged along an outer circumferential surface of said plunger; and
a flange assembly including first and second flange members, wherein
said first and second flange members are symmetrical, said first and second flange members each include a cutout, and the two cutouts loin together to form a window that displays at least one of said plurality of numerical indicators.

2. The syringe according to claim 1, wherein
at least a portion of an interior surface of said body includes said first portion of said body, and said thread has a saw tooth profile to facilitate rotation of said plunger with respect to said body to set said dose and axial movement of said plunger with respect to said body to dispense said set dose.

3. The syringe according to claim 2, wherein
said plunger is pushed axially into said body to selectively dispense said medicament from said body.

4. The syringe according to claim 2, wherein
said at least first portion of said plunger is pushed axially into said body in said second direction to selectively dispense an amount of said medicament drawn into said body based on said rotation.

5. The syringe according to claim 1, wherein
a needle is connected to said body to facilitate at least one of drawing in and dispensing of said medicament.

6. The syringe according to claim 1, wherein
said medicament is drawn into said syringe body as said first portion of said plunger is being rotated to set said dose.

7. The syringe according to claim 1, wherein
said first direction is opposite to said second direction.

8. The syringe according to claim 1, wherein
said first portion of said body includes a threaded nut assembly, and
said thread includes a profile matching a pitch of said threaded nut assembly.

9. The syringe according to claim 1, wherein
said plurality of numerical indicators is disposed along said thread.

10. The syringe according to claim 1, wherein the first and second flange members include inner threads that engage the threads on the plunger.

11. A syringe, comprising:
a body for receiving a medicament;
a flange assembly including a flange, a wall extending from said flange into said body, a bore extending through said flange assembly and first and second flange members, said first and second flange members are symmetrical; and
a plunger rotatably movable with respect to said bore of said flange assembly to selectively set a dose of said medicament and axially movable with respect to said body to selectively draw in or dispense said medicament according to said dose, wherein:
said bore of said flange assembly and said plunger have corresponding threaded portions to facilitate rotating said plunger with respect to said flange assembly to draw said dose of said medicament into said body;

said threaded portion of said plunger axially deflects with respect to said threaded portion of said bore of said flange assembly when said plunger is pushed axially through said flange assembly to dispense said medicament from said body; and
a plurality of numerical indicators is helically arranged along an outer circumferential surface of said threaded portion of said plunger, wherein
said first and second flange members each include a cutout, and the two cutouts loin together to form a window that displays at least one of said plurality of numerical indicators.

12. The syringe according to claim 11, wherein
said body has a first portion having a first diameter and a second portion having a second diameter, said first diameter being larger than said second diameter.

13. The syringe according to claim 12, wherein
the medicament is received in said second portion of said body.

14. The syringe according to claim 11, wherein
a needle is connected to said body to facilitate at least one of drawing in and dispensing of said medicament.

15. The syringe according to claim 14, wherein
a shield is connected to said body to cover said needle.

16. The syringe according to claim 12, wherein
said plunger is movable between first and second positions, when said plunger is in said first position first and second seal members of said plunger are disposed in said second portion of said body, and when said plunger is in said second position said first seal member is in said second portion and said second seal member is in said first portion of said body.

17. The syringe according to claim 11, wherein
said medicament is drawn into said syringe body with said plunger is configured for continuous rotation to set said dose.

* * * * *